United States Patent [19]

Miyake et al.

[11] Patent Number: 5,329,031

[45] Date of Patent: Jul. 12, 1994

[54] METALLOCENE AND PROCESS FOR PRODUCING POLYOLEFIN USING THE SAME

[75] Inventors: Shigenobu Miyake; Nobuyuki Kibino; Takashi Monoi; Hiroyuki Ohira; Shintaro Inazawa, all of Oita, Japan

[73] Assignee: Showa Denko K.K., Tokyo, Japan

[21] Appl. No.: 982,894

[22] Filed: Nov. 30, 1992

[30] Foreign Application Priority Data

Nov. 28, 1991 [JP] Japan .................................. 3-314978
Dec. 3, 1991 [JP] Japan .................................. 3-319275
May 7, 1992 [JP] Japan .................................. 4-114985
Sep. 4, 1992 [JP] Japan .................................. 4-237393

[51] Int. Cl.$^5$ ............................................ C07F 7/02
[52] U.S. Cl. ........................................ 556/12; 556/9; 556/11; 556/51; 556/52; 556/53; 556/28; 502/152; 526/127; 526/160
[58] Field of Search ................. 526/126, 160; 556/9, 556/11, 12, 51, 52, 53, 28

[56] References Cited

U.S. PATENT DOCUMENTS

| | | | |
|---|---|---|---|
| 5,017,714 | 5/1991 | Welborn, Jr. | 556/12 |
| 5,071,808 | 12/1991 | Antberg et al. | 502/117 |
| 5,126,303 | 6/1992 | Resconi et al. | 502/117 |
| 5,132,262 | 7/1992 | Rieger et al. | 502/117 |

FOREIGN PATENT DOCUMENTS

| | | |
|---|---|---|
| 63-295607 | 12/1988 | Japan . |
| 1301704 | 12/1989 | Japan . |
| 1319489 | 12/1989 | Japan . |
| 275609 | 3/1990 | Japan . |
| 275610 | 3/1990 | Japan . |
| 276887 | 3/1990 | Japan . |

OTHER PUBLICATIONS

*Chemistry Letters*, Excellent Stereoregular Isotactic Polymerizatioins of Propylene with $C_2$-Symmetric Siliylene-Bridged Metallocene Catalysts, Takaya Mise et al., pp. 1853-1856, 1989.
*J. Am. Chem. Soc.*, vol. 109, pp. 6544-6545, 1987.
*J. Am. Chem. Soc.*, vol. 106, pp. 6355-6364, 1984.
*J. Am. Chem. Soc.*, vol. 110, pp. 6255-6256, 1988.
*Polymer Preprints*, Japan, vol. 40, p. 265, 1991.
*Organometallics*, vol. 10, pp. 2061-2068, 1991.

Primary Examiner—Joseph L. Schofer
Assistant Examiner—David Wu
Attorney, Agent, or Firm—Sughrue, Mion, Zinn, Macpeak & Seas

[57] ABSTRACT

A metallocene having an asymmetric ligand which is represented by the formula below and its enantiomer:

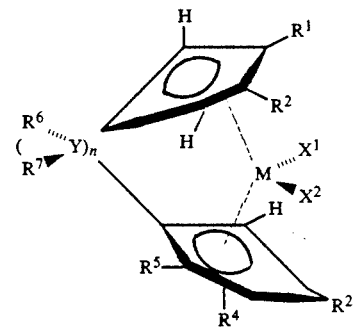

and a process for producing a polyolefin using the same as a catalyst component. The metallocene and its enantiomer are particularly effective in the production of highly stereospecific polyolefins.

7 Claims, 4 Drawing Sheets

METALLOCENE AND PROCESS FOR PRODUCING POLYOLEFIN USING THE SAME

FIELD OF THE INVENTION

This invention relates to a novel metallocene having a crosslinked ligand having an asymmetric substituent and to a process for producing a polyolefin using the same as a catalyst.

BACKGROUND OF THE INVENTION

Kaminsky's catalyst (metallocene/methylaluminoxane) is widely known as a homogeneous catalyst for olefin polymerization. This catalyst system is characterized by its markedly high activity per unit transition metal thereof. Among metallocenes which are widely known and have been classically used is bis(cyclopentadienyl)zirconium dichloride (zirconocene dichloride). Kaminsky et al proposed to copolymerize ethylene and an α-olefin using a catalyst system composed of zirconocene dichloride and methylaluminoxane as disclosed in JP-A-58-19303 (the term "JP-A" as used herein means an "unexamined published Japanese patent application"). However, the above catalyst system is disadvantageous in that it is difficult to obtain a copolymer having a sufficiently high molecular weight in an industrially advantageous temperature range (50° to 70° C.) and that a large quantity of a comonomer must be charged in a polymerization system in order to obtain a linear low-density polyethylene having a desired density.

Ewen et al succeeded in obtaining a high-molecular-weight copolymer in a preferred temperature range (50° to 70° C.) by using a metallocene having a substituent on the cyclopentadienyl ligand (see JP-A-60-35007). However, the technique involves a problem from an industrial view point because very expensive methylaluminoxane must be used in a large quantity as a co-catalyst.

Further, Welborn et al proposed to increase the polymerization activity per unit aluminoxane by supporting a metallocene and aluminoxane on a porous inorganic metal oxide (see JP-A-61-296008). The polymerization activity reached, however, is not sufficiently high. Besides, the polymerization activity of the catalyst system is decreasing with time immediately after contact between a metallocene and aluminoxane.

Furthermore, Ishihara et al proposed to use a co-catalyst composed of methylaluminoxane and other organoaluminum compound in an attempt to increase the polymerization activity per aluminoxane (see JP-A-60-130604 and JP-A-60-260602). However, the effect obtained is not so high as expected.

It has recently been revealed that use of a Kaminsky's catalyst in polymerization of α-olefins, chiefly propylene, enables stereospecific polymerization. For example, it is reported that atactic polypropylene (*Macromol. Chem. Rapid Commun.*, Vol. 4, pp. 417-421 (1983), JP-A-58-19309), isotactic polypropylene (*Angew. Chem. Int. Ed. Engl.*, Vol. 24, pp. 507-508 (1983), *J. Am. Chem. Soc.*, Vol. 106, p. 6355 (1984), *J. Am. Chem. Soc.*, Vol. 109, p. 6544 (1987), *Chem. Lett.*, pp. 1853-1856 (1989), JP-A-2-76887), and syndiotactic polypropylene (*J. Am. Chem. Soc.*, Vol. 110, p. 6255 (1988)) can be prepared. The ligand structure and stereostructure of metallocenes are key points for manifestation of stereospecificity in these polymerization systems.

However, metallocenes which make it possible to produce industrially important isotactic polypropylene are very limited in kind and performance. For example, ethylenebis(η5-indenyl)zirconium dichloride or ethylenebis(η5-tetrahydroindenyl)zirconium dichloride disclosed in JP-A-63-295607 enables production of isotactic polypropylene in the presence of methylaluminoxane, but the stereospecificity of the isotactic polypropylene obtained is relatively low as about 95% in terms of mm %. Moreover, the resulting polymer has a melting point as low as 135°-146° C. because of the occurrence of hydrogen shift polymerization in the polymer chain, called 1,3-insertion (see *Macromol. Chem., Rapid Comun.*, Vol. 8, p. 305 (1987)).

JP-A-2-75609 and JP-A-2-75610 describe that an isoblock polymer is obtained by polymerization of propylene in the presence of indenyl(cyclopentadienyl)(dimethylsilyl)hafnium and methylaluminoxane. The polymer obtained here is a soft polymer having a low melting point and low stereospecificity (mm %), differing from so-called isotactic polypropylene of industrial importance.

Ishihara et al. report production of isotactic polypropylene by the use of (CHI)HfCl$_2$ (*Polymer Preprints, Japan*, Vol. 40, p. 265 (1991)), but the polymer obtained has a very low mm %.

It is reported in JP-A-1-301704, JP-A-1-319489, JP-A-2-76887, and *Chem. Lett.*, pp. 1853-1856 (1989) that dimethylsilylbis(2,3,5-trimethylcyclopentadienyl)zirconium dichloride enables production of isotactic polypropylene in the co-presence of methylaluminoxane, achieving stereospecificity as high as 99 mm % or more. It turned out, however, that the polymer chain contains chemical inversion, which is a polymer chain defect resulting from inversion of the direction of monomer insertion and which reduces rigidity of the polymer (see *KOBUNSHI KAKO*, Vol. 41, p. 28 (1992)). In addition, the greatest problem associated with this catalyst system resides in that the above zirconium complex includes from the nature of its structure two stereoisomers, a racemic modification and a meso form, and that it is only the racemic modification that enables production of highly isotactic polypropylene. The other isomer, a meso form, catalyzes formation of atactic polypropylene with non-negligible activity. Therefore, the preparation of the complex involves a complicated purification step for complete removal of the meso form and thus incurs increased cost.

Collins et al report that isotactic polypropylene is prepared in the presence of a combination of bis(t-butylcyclopentadienyl)zirconium dichloride and methylaluminoxane (see Organometallics, Vol. 10, p. 2061 (1991)). In this case, too, it is necessary to separate a racemic mixture from an undesired meso form in the preparation of the zirconium complex.

SUMMARY OF THE INVENTION

An object of the present invention is to provide a novel and useful metallocene free from the above-mentioned problems associated with the conventional techniques.

Another object of the present invention is to provide an economical process for producing a polyolefin using a metallocene catalyst.

As a result of extensive investigations, the inventors have succeeded in synthesizing novel metallocenes shown below with good efficiency and have found that the novel metallocenes, which embrace no meso form from their structural nature are extremely useful as a component of a catalyst system for stereospecific polymerization of olefins, thus having reached the present invention.

The present invention relates to a metallocene represented by formula (I) and its enantiomer:

(I)

wherein M represents a transition metal selected from Ti, Zr, and Hf; $X^1$ and $X^2$, which may be the same or different, each represents a hydrogen atom, a hydrocarbon group containing from 1 to 10 carbon atoms, an alkylsilyl group, an arylsilyl group, or a halogen atom; $R^1$, $R^2$, $R^3$, $R^6$, and $R^7$ each represents a hydrogen atom, a hydrocarbon group containing from 1 to 10 carbon atoms, an alkylsilyl group, or an arylsilyl group, provided that either one of $R^1$ and $R^2$ is not a hydrogen atom; $R^4$ and $R^5$ each represents a hydrocarbon group containing from 1 to 10 carbon atoms, an alkylsilyl group, or an arylsilyl group, or they are connected together to form a ring; Y represents a-carbon atom, a silicon atom, or a germanium atom; and n represents an integer of from 1 to 3.

The present invention also relates to a process for producing a polyolefin comprising polymerizing an olefin in the presence of a metallocene represented by formula (I) or its enantiomer as a catalyst.

DETAILED DESCRIPTION OF THE INVENTION

While the metallocenes of the present invention include not only those represented by formula (I) and formulae (II) and (III) described later but also their enantiomers, the present invention will be hereinafter explained with reference to those of formulae (I), (II) and (III) representatively.

Of the metallocenes represented by formula (I), those wherein Y is a carbon atom are preferred. More preferred are those wherein Y is a carbon atom; and $R^4$ and $R^5$ are connected to each other to form a ring, and particularly an indenyl ring, that is, compounds represented by formula (II):

(II)

wherein M, $X^1$, $X^2$, $R^1$, $R^2$, $R^3$, $R^6$, $R^7$, and n are as defined above; and Y' represents a carbon atom.

In formulae (I) and (II), M is preferably Zr or Hf. Included in preferred metallocenes of formula (I) wherein M is Zr are those represented by formula (III):

(III)

wherein $X^1$, $X^2$, $R^1$, $R^2$, $R^3$, $R^6$, and $R^7$ are defined above; and Y' represents a carbon atom.

Metallocenes of formula (III) wherein Zr is replaced with Hf are also preferred.

All the compounds represented by formulae (I) through (III) are novel metallocenes having an asymmetric ligand. In these metallocenes, the substituents on each cyclopentadienyl ring at the respective positions as specified in the formulae (i.e., those represented by $R^1$ to $R^5$) are selected from hydrocarbon groups having from 1 to 10 carbon atoms (e.g., alkyl, aryl, alkylaryl, and arylalkyl groups), alkylsilyl groups (e.g., trialkylsilyl groups) and arylsilyl groups (e.g., triarylsilyl groups), and preferably selected from those which are more bulky than a methyl group, such as a t-butyl group.

While not limiting, the compounds of formula (I) can be synthesized through the following synthetic routes:

(1)

In the above schemes, nBt is a normal butyl group, tBu is a t-butyl group, and THF is tetrahydrofuran.

The reactions shown by schemes (1) and (2) are to introduce a substituent onto the indene ring or the cyclopentadiene ring and are carried out by generating an indenyl anion or a cyclopentadienyl anion in a dry THF using an alkali metal, followed by reacting the anion with a halogenated alkyl compound at room temperature to 80° C. The reaction of scheme (3) is to form a fulvene, wherein a cyclopentadienyl anion is generated in a dry THF using an alkali metal and is reacted with a ketone. The reaction of scheme (4) is to bond the indene compound obtained by the reaction of scheme (1) and the fulvene compound produced through the reactions of schemes (2) and (3), wherein an indenyl anion is generated in a dry THF using an alkali metal and is reacted with the fulvene compound. The reaction of scheme (5) is to form a coordination compound of the present invention, wherein a dianion (ligand) of the compounds obtained by the reaction of scheme (4) is generated in a dry THF and is reacted with a halogenated metal at a temperature of not higher than −20° C.

Processes for preparing bis(substituted cyclopentadienyl) bridged bidendate having a crosslinked structure as shown in scheme (4) are known, as described in *J. Am. Chem. Soc.*, Vol. 110, pp. 976–978 (1988) and ibid, Vol. 107, pp. 8103–8110 (1985).

Specific examples of the metallocenes according to the present invention are shown below. In the following nomenclature, the positions of substituents on cyclopentadienyl rings for $R^1$, R2, $R^3$, $R^4$ and $R^5$ in formula (I) are the 3-, 4-, 3'-, 4'- and 5'- positions, respectively.

Examples of the zirconocenes of formula (I) wherein M is zirconium are ethylene(4-methylcyclopentadienyl)(3'-methylindenyl)zirconium dichloride, ethylene(4-t-butylcyclopentadienyl)(3'-methylindenyl)zirconium dichloride, ethylene(4-t-butylcyclopentadienyl)(3'-t-butylindenyl)zirconium dichloride, ethylene(4-methylcyclopentadienyl)(3'-t-butylindenyl)zirconium dichloride, ethylene(4-methylcyclopentadienyl)(3'-trimethylsilylindenyl)zirconium dichloride, isopropylidene(4-methylcyclopentadienyl)(3'-methylindenyl)zirconium dichloride, isopropylidene(4-t-butylcyclopentadienyl)(3'-methylindenyl)zirconium dichloride, isopropylidene(4-t-butylcyclopentadienyl)(3'-t-butylindenyl)zirconium dichloride, dimethylsilylene(4-methylcyclopentadienyl)(3'-methylindenyl)zirconium dichloride, dimethylsilylene(4-t-butylcyclopentadienyl)(3'-methylindenyl)zirconium dichloride, dimethylsilylene(4-t-butylcyclopentadienyl)(3'-t-butylindenyl)zirconium dichloride, isopropylidene(4 -methylcyclopentadienyl)(3',4',5'-trimethylcyclopentadienyl)zirconium dichloride, isopropylidene(4-t-butylcyclopentadienyl)(3',4',5'-trimethylcyclopentadienyl)zirconium dichloride, isopropylidene(4-t-butylcyclo-pentadienyl)( 3',4',5'-tri-t-butylcyclopentadienyl)zirconium dichloride, isopropylidene(4-methylcyclopentadienyl)(3'-methylindenyl)zirconium dimethyl, isopropylidene(4-t-butylcyclopentadienyl)(3'-methylindenyl)zirconium dimethyl, and isopropylidene(4-t-butylcyclopentadienyl)(3'-t-butylindenyl)zirconium dimethyl.

Specific examples of hafnocenes of formula (I) wherein M is hafnium are ethylene(4-methylcyclopentadienyl)(3'-methylindenyl)hafnium dichloride, ethylene(4-t-butylcyclopentadienyl)(3'-methylindenyl)hafnium dichloride, ethylene(4-t-butylcyclopentadienyl)(3'-t-butylindenyl)hafnium dichloride, ethylene(4-methylcyclopentadienyl)(3'-t-butylindenyl)hafnium dichloride, ethylene(4-methylcyclopentadienyl)(3'-trimethylsilylindenyl)hafnium dichloride, isopropylidene(4-methylcyclopentadienyl)(3'-methylindenyl)hafnium dichloride, isopropylidene(4-t-butylcyclopentadienyl)(3'-methylindenyl)hafnium dichloride, isopropylidene(3-t-butylcyclopentadienyl)(3'-t-butylindenyl)hafnium dichloride, isopropylidene(4-t-butylcyclopentadienyl)(3'-t-butylindenyl)hafnium dichloride, dimethylsilylene(4-methylcyclopentadienyl)(3'-methylindenyl)hafnium dichloride, dimethylsilylene(4-t-butylcyclopentadienyl)(3'-methylindenyl)hafnium dichloride, dimethylsilylene(4-t-butylcyclopentadienyl)(3+-t-butylindenyl)hafnium dichloride, and isopropylidene(4-methylcyclopentadienyl)( 3',4',5'-trimethylcyclopentadienyl)hafnium dichloride.

While these metallocenes respectively include two stereoisomers each of which including respective optical isomers, the ligand has such a structure as providing no meso form which catalyzes production of atactic polypropylene. It is important that one of the two stereoisomers should have a considerably low activity or be inactive.

For example, the zirconocene of formula (III) includes two stereoisomers as shown by the following formulas (IV)-A and (IV)-B, each of which is a racemic modification but not a meso form.

wherein $R^1$, $R^2$, $R^3$, $R^6$, $R^7$, $X^1$, $X^2$, and $Y'$ are as defined above.

It has been ascertained that isomer (B) (the metallocenes of formula (I) wherein $R^1$ is a hydrogen atom) catalyzes production of highly isotactic polyolefins, whereas isomer (A) (those wherein $R^2$ is a hydrogen atom) has no or very low polymerization activity and produces no substantial atactic polyolefin. Therefore, a highly isotactic polyolefin can be produced even if the metallocene used as a catalyst component is a mixture of isomers (A) and (B). That is, there is no need to remove isomer (A) in the preparation of the complex. This is a point greatly different from the conventional metallocenes and is thus characteristic of the present invention.

While other catalyst components to be used in olefin polymerization are not particularly limited, organoaluminumoxy compounds are preferably used. Examples of suitable organoaluminumoxy compounds include partial hydrolysis products of organoaluminum compounds (e.g., trialkylaluminum and dialkylaluminum dichloride). In particular, aluminoxane compounds represented by formula (V) or (VI) are particularly preferred.

wherein the plurality of $R^8$ may be the same or different and each represents a hydrocarbon group such as an alkyl group (e.g., methyl, ethyl, propyl, butyl, or isobutyl, and preferably methyl); and m represents an integer of from 4 to 100, preferably 6 or greater, and more preferably 10 or greater.

Processes for preparing these aluminoxane compounds are well known as described in H. Sinn, *Transition Metals and Organometallics as Catalysts for Olefin Polymerization*, p.257, ed. by W. Kaminsky and H. Sinn, Springer Verlag, Berlin (1988). For example, they may be obtained by adding a trialkylaluminum to a suspension of a crystal water-containing salt (e.g., copper sulfate hydrate or aluminum sulfate hydrate) in a hydrocarbon solvent.

Olefins which may be polymerized according to the process of the present invention include olefins, cyclic olefins and dienes, such as propylene, 1-butene, 2-butene, 1-pentene, 4-methyl-l-pentene, cyclopentene, norbornene, cyclopentadiene, butadiene, 1,5-hexadiene, and 1,4-hexadiene. These olefins may be used either individually or as a mixture of two or more thereof. The present invention is particularly advantageous in the polymerization of olefins having 3 or more carbon atoms.

The polymerization may be carried out by any of liquid phase polymerization, slurry polymerization and gas phase polymerization. Solvents to be used in liquid phase polymerization include hydrocarbon solvents capable of dissolving both the metallocene and organoaluminumoxy compound, such as aromatic hydrocarbons, e.g., benzene, toluene, o-xylene, m-xylene, p-xylene, ethylbenzene, butylbenzene, mesitylene, and chlorobenzene, with toluene and xylene being preferred.

The metallocene and organoaluminumoxy compound may be supplied to a reaction system either separately or in the form of a mixture thereof. The metallocene of the present invention may also be used as being supported on a carrier, such has silica, alumina, or magnesium chloride.

The concentration of the metallocene having the catalytic activity (i.e., isomer (B)) in a reaction solution (including a solvent) of the reaction system is not particularly limited, and it is preferably used in an amount of from $10^{-10}$ to $10^{-3}$ mol/l, with the Al/M molar ratio (M: Ti, Zr and Hf) being 10 or more, and particularly 100 or more.

While the olefin pressure of the reaction system and the polymerization temperature are not critical, it is preferred to carry out the reaction at a temperature of from −30° to 200° C., more preferably from 0° to 80° C., and most preferably from 50 to 70° C., at an olefin pressure of from normal pressure to 50 kg/cm$^2$. Molecular weight control during the polymerization can be effected by any known means, such as proper selection of a reaction temperature or hydrogen introduction.

Copolymerization of ethylene and an α-olefin is a preferred embodiment of the present invention. In this embodiment, the metallocene and organoaluminumoxy compound are employed in the form of a solid catalyst supported on an inorganic oxide carrier together with an organoaluminum compound (other than organoaluminumoxy compounds) as a co-catalyst thereby to exhibit extremely effective catalyzing performance.

While not limiting, the inorganic oxide as a carrier includes silica, alumina, magnesia, aluminosilicate, boron oxide, and calcium oxide. The above inorganic oxide carrier having been sintered at a high temperature and treated with an organoaluminum compound is preferred.

While not limiting, the amounts of the metallocene and the organoaluminumoxy compound to be supported on the inorganic oxide carrier preferably range from 0.05 to 10% by weight and from 0.01 to 70% by weight, and more preferably from 0.5 to 5% by weight and from 0.01 to 30% by weight, respectively, based on the carrier.

While not limiting, the organoaluminum compound which can be used as a co-catalyst preferably includes trialkylaluminum compounds, and particularly triisobutylaluminum, trimethylaluminum, and trioctylaluminum. The concentration of the organoaluminum compound in a reaction solution of the reaction system is usually from 0.001 to 1 mmol/l in terms of aluminum. The organoaluminum compound may be premixed with the metallocene-carried solid catalyst immediately before polymerization.

α-Olefins which are copolymerized with ethylene according to the above-mentioned preferred embodiment of the present invention include olefins, cyclic olefins and dienes, such as propylene, 1-butene, 1-pentene, 1-hexene, 1-heptene, 1-octene, 1-decene, 4-methyl-1-pentene, cyclopentene, cyclopentadiene, butadiene, 1,5-hexadiene, 1,4-hexadiene, and 1,4-pentadiene. These comonomers may be used either individually or in combination of two or more thereof.

The molar ratio of ethylene to α-olefin in the ethylene copolymer is not particularly limited but preferably ranges from 0.5/1 to 10000/1, and particularly from 10/1 to 1000/1. The possible lowest density that the resulting copolymer may have is 0.80. Ethylene copolymers having a density of from 0.89 to 0.94 are preferably used.

The copolymerization may be carried out by any of liquid phase polymerization, slurry polymerization and gas phase polymerization, and preferably slurry polymerization in isobutane or gas phase polymerization. Multi-stage polymerization is also feasible. Size control of the ethylene copolymer may be effected by prepolymerization of the olefins. While the ethylene pressure of the reaction system is not particularly limited, it is preferably from normal pressure to 1000 Kg/cm$^2$ and more preferably from 1 to 40 Kg/cm$^2$.

According to the above-described preferred embodiment, the catalyst system exhibits high activity per unit co-catalyst and undergoes no change in activity with time, and an ethylene-α-olefin copolymer having a low melting point, high transparency, and a narrow composition distribution can be produced.

The present invention is now illustrated in greater detail with reference to Examples, but it should be understood that the present invention is not deemed to be limited thereto.

An NMR analysis on the polyolefin produced was conducted with "EX-400" manufactured by Japan Electron Optics Laboratory Co., Ltd. Stereospecificity of the polyolefins obtained was determined from the $^{13}$C-NMR spectrum and evaluated in terms of intensity ratio of mm, mr, and rr signals. The proportion of triad unit in the polyolefin molecular chain is given in terms of "mm %". Absorption peaks of the NMR spectrum were assigned according to *Macromolecules*, Vol. 8, p.687 (1975).

The molecular weight of the polyolefins obtained was estimated through gel-permeation chromatography using "waters-150C" and a column "Shodex".

Physical properties of the ethylene-α-olefin copolymers obtained were measured through an FT-IR analysis using "Perkin-Elmer 1720X" and differential thermal analysis using "Perkin-Elmer DSC-7".

The molecular weight of the ethylene-α-olefin copolymers obtained was evaluated in terms of a melt flow rate (hereinafter abbreviated as MFR) as measured at 190° C. under a load of 2.16 kg in accordance with JIS K-6760. High-load melt index (hereinafter abbreviated as HLMI) of the copolymers was measured under a load of 21.6 kg.

The ratio of an α-olefin in the ethylene-α-olefin copolymers (hereinafter abbreviated as SCB) was expressed by the number of branches in the polymer main chain as determined by the FT-IR analysis. Specifically, the number of branches per 1000 carbon atoms in the polymer main chain was calculated from a ratio of the peak height at 1380 cm$^{-1}$ of the IR spectrum of a sample copolymer to that at 4250 cm$^{-1}$ of the IR spectrum of polyethylene having no branching.

EXAMPLE 1

Preparation of Isopropylidene(4-methylcyclopentadienyl)(3'-t-butylindenyl)zirconium Dichloride All the reactions were carried out in an inert gas atmosphere, and the reactor used had been dried beforehand.

In a 300 ml glass-made reactor was charged 100 ml of dry tetrahydrofuran (THF), and 3 g of dimethyl(4-methylcyclopentadienyl)(3'-t-butylindenyl)methane was dissolved therein. To the solution was added 15 ml of a 1.6 mol/l hexane solution of n-butyl lithium under cooling with ice. After the mixture was allowed to react at room temperature for 1 hour, THF was removed by distillation under reduced pressure. To the residue was added 50 ml of methylene chloride while cooling. A suspension of 2.63 g of zirconium tetrachloride in 50 ml of methylene chloride, which had been prepared in a separate flask, was cooled, and the above-prepared suspension of dimethyl(4-methylcyclopentadienyl)(3'-t-butylindenyl)methane lithium salt was added thereto while being cooled through a cannula, followed by reacting at room temperature for 2 hours. Lithium chloride thus formed was removed, and the residual solution was concentrated, followed by recrystallization from toluene several times, whereby 0.8 g of the titled complex was obtained as a crystal.

Elementary Analysis for $C_{22}H_{26}ZrCl_2$: Calcd. (%): C 58.39; H 5.79; Found (%): C 58.30; H 5.77.

Polymerization

In a 1.5 l SUS-made autoclave having been thoroughly purged with nitrogen were successively charged 300 ml of purified toluene, 15 ml of a toluene solution containing 2.7 mol/l (in terms of aluminum) of methylaluminoxane (produced by TOSO AKUZO CO., LTD.), and 0.02 mmol of the above-prepared zirconocene, followed by cooling to 3° C. Then, 2 mols of propylene was poured thereinto, and polymerization was conducted for 1 hour. The catalyst components were decomposed with methanol, and the residue was dried to recover 37 g of highly isotactic polypropylene.

mm %: 99.1%. Molecular Weight: 102000; Melting Point: 162° C.

EXAMPLE 2

Preparation of Isopropylidene(4-t-butylcyclopentadienyl)(3'-t-butylindenyl)zirconium Dichloride All the following reactions were carried out in an inert gas atmosphere, and the reactor used had been dried beforehand.

In a 300 ml glass-made reactor was charged 100 ml of dry THF, and 3 g of dimethyl(4-butylcyclopentadienyl)(3'-t-butylindenyl)methane was dissolved therein. To the solution was added 15 ml of a 1.6 mol/l hexane solution of n-butyl lithium under cooling with ice. After the mixture was allowed to react at room temperature for 1 hour, THF was removed by distillation under reduced pressure. To the residue was added 50 ml of methylene chloride while cooling. A suspension of 2.63 g of zirconium tetrachloride in 50 ml of methylene chloride, which had been prepared in a separate flask, was cooled, and the above-prepared suspension of dimethyl(4-butylcyclopentadienyl)(3'-t-butylindenyl)methane lithium salt was added thereto while being cooled through a cannula, followed by reacting at room temperature for 2 hours. Lithium chloride thus formed was removed, and the residual solution was concentrated, followed by recrystallization from toluene several times, whereby 0.3 g of the titled zirconocene was obtained as an orange crystal.

Elementary Analysis for $C_{25}H_{32}ZrCl_2$: Calcd. (%): C 60.78; H 6.53; Found (%): C 60.81; H 6.48.

Figure 1:
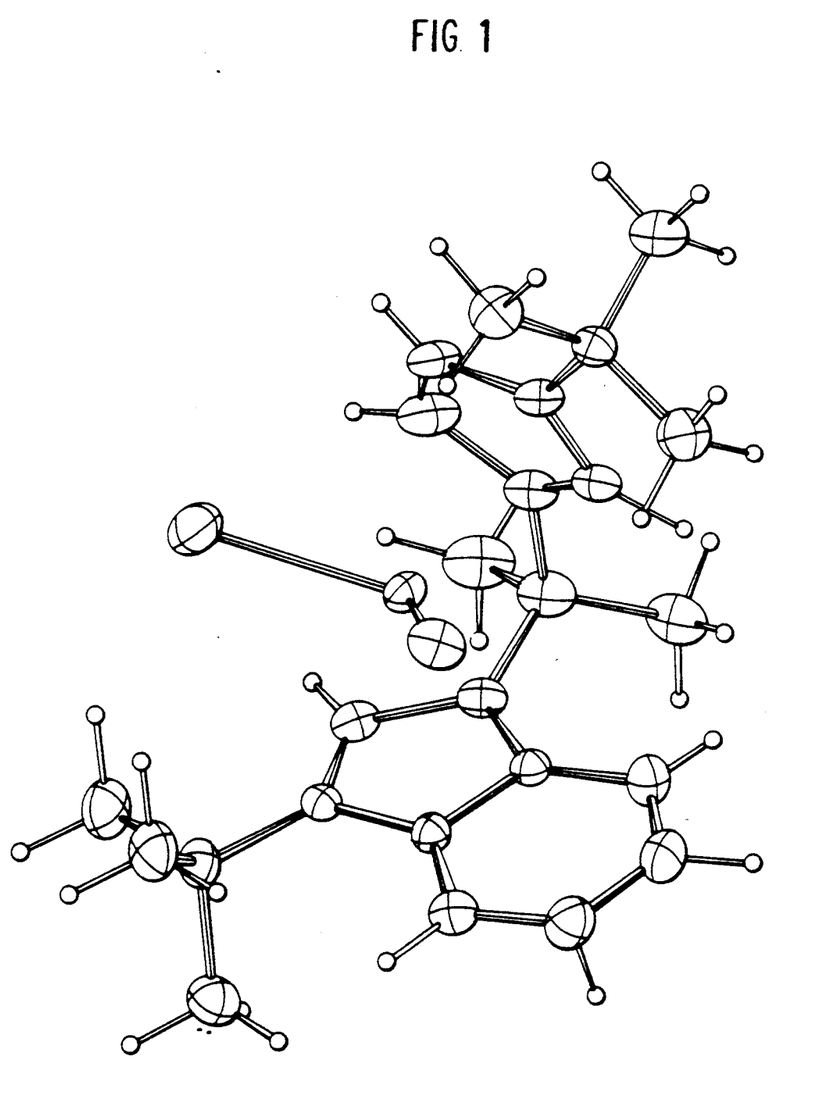
FIG. 1 is an Ortep diagram of the metallocene prepared in Example 2 obtained by X-ray crystallography.

The Ortep diagram of the crystal obtained by X-ray crystallography is shown in FIG. 1.

Figure 2:
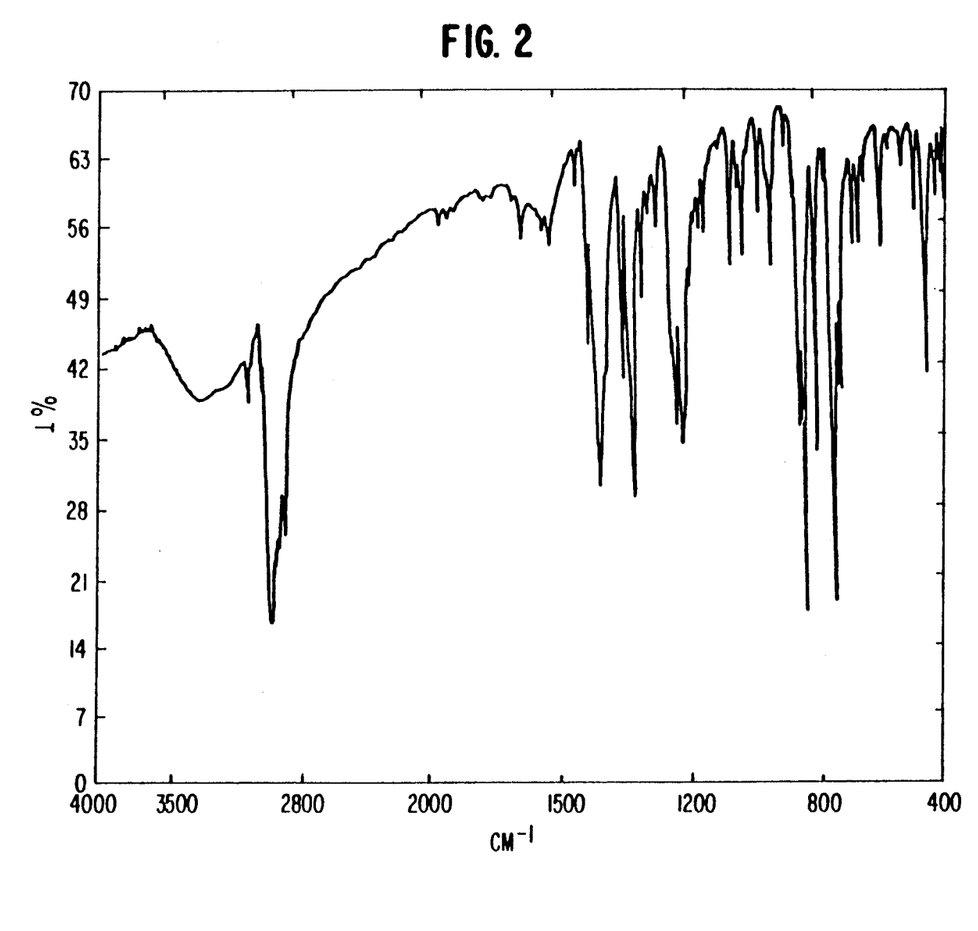
FIG. 2, 3 and 4 are the IR spectrum, the $^1$H-NMR spectrum, and the mass spectrum, respectively, of the metallocene prepared in Example 2.
Figure 3:
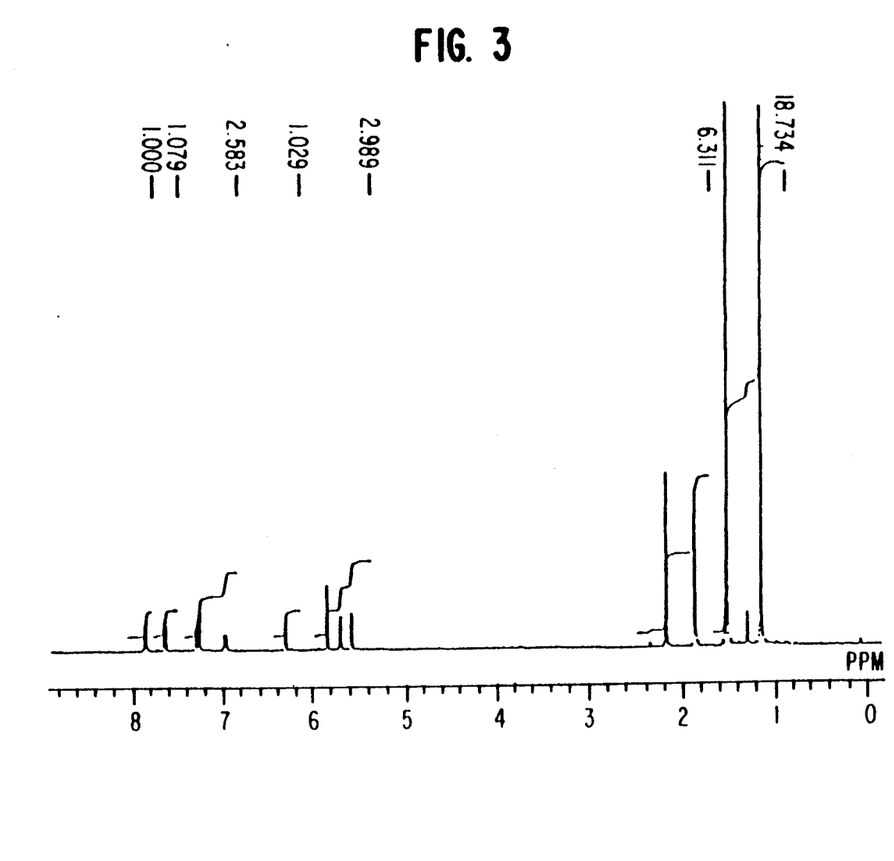
Figure 4:
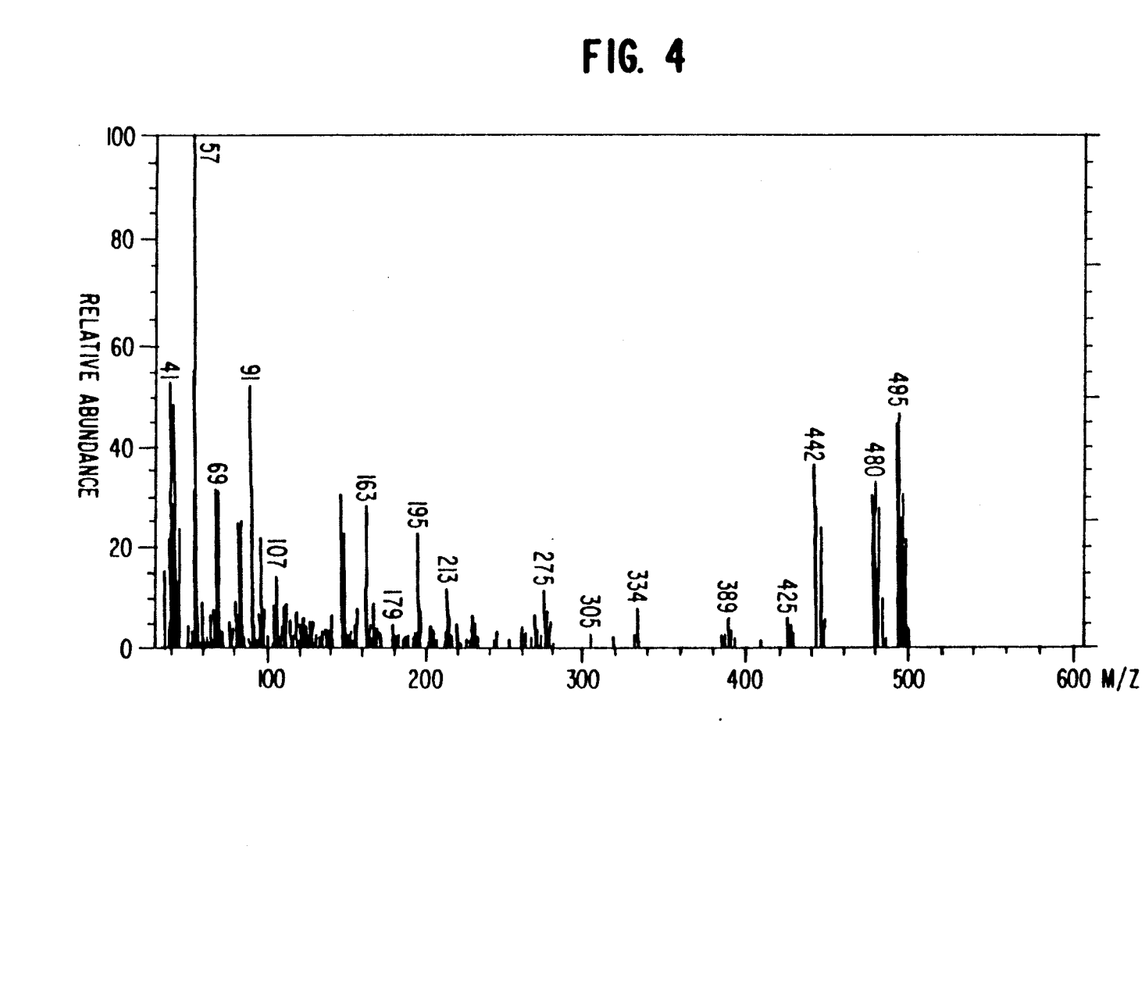

The IR spectrum of the crystal was measured according to the KBr method using an IR analyzer "Perkin-Elmer 5150" and it is shown in FIG. 2. The $^1$H-NMR spectrum of the crystal (in CDCl$_3$) was also measured using the NMR analyzer "EX-400" and shown in FIG. 3. Further, the mass spectrum was measured according to the direct introduction method using a mass spectrometer "JMS-AX500" manufactured by Japan Electron Optics Laboratory Co., Ltd. and it is shown in FIG. 4.

Polymerization

In a 1.5 l SUS-made autoclave having been thoroughly purged with nitrogen were successively charged 300 ml of purified toluene, 15 ml of a toluene solution containing 2.7 mol/l (in terms of aluminum) of methylaluminoxane (produced by TOSO AKUZO CO., LTD.), and 0.02 mmol of the above-prepared zirconocene, followed by cooling to 3° C. Then, 2 mols of propylene was poured thereinto, and polymerization was conducted for 1 hour. The catalyst components were decomposed with methanol, and the residue was dried to recover 40 g of highly isotactic polypropylene.

mm %: 99.6%; Molecular Weight: 160000; Melting Point: 164° C.

EXAMPLE 3

Preparation of Isopropylidene(4-t-butylcyclopentadienyl/(3'-t-butylindenyl)hafnium Dichloride All the reactions were carried out in an inert gas atmosphere, and the reactor used had been dried beforehand.

In a 300 ml glass-made reactor was charged 100 ml of dry THF, and 3 g of dimethyl(4-t-butylcyclopentadienyl)(3'-t-butylindenyl)methane was dissolved therein. To the solution was added 15 ml of a 1.6 mol/l hexane solution of n-butyl lithium under cooling with ice. After the mixture was allowed to react at room temperature for 1 hour, THF was removed by distillation under reduced pressure. To the residue was added 50 ml of methylene chloride while cooling. A suspension of 3.0 g of hafnium tetrachloride in 50 ml of methylene chloride, which had been prepared in a separate flask, was cooled, and the above-prepared suspension of dimethyl(4-t-butylcyclopentadienyl)(3'-t-butylindenyl)methane lithium salt was added thereto while being cooled through a cannula, followed by reacting at room temperature for 2 hours. Lithium chloride thus formed was removed, and the residual solution was concentrated, followed by recrystallization from toluene several times, whereby 0.35 g of the titled complex was obtained as a crystal.

Elementary Analysis for $C_{25}H_{32}HfCl_2$: Calcd. (%): C 51.60; H 5.54; Found (%): C 51.42; H 5.32.

Polymerization

In a 1.5 l SUS-made autoclave having been thoroughly purged with nitrogen were successively charged 300 ml of purified toluene, 15 ml of a toluene solution containing 2.7 mol/l (in terms of aluminum) of methylaluminoxane (produced by TOSO AKUZO CO., LTD.), and 0.02 mmol of the above-prepared hafnocene, followed by cooling to 3° C. Then, 2 mols of propylene was poured thereinto, and polymerization was conducted for 1 hour. The catalyst components were decomposed with methanol, and the residue was dried to recover 35 g of highly isotactic polypropylene.

mm %: 99.6%; Molecular Weight: 260000.

COMPARATIVE EXAMPLE 1

Propylene was polymerized in the same manner as in Example 1, except for replacing isopropylidene(4-methylcyclopentadienyl)(3'-t-butylindenyl)zirconium dichloride with ethylenebis(indenyl)zirconium dichloride. There was obtained 40 g of isotactic polypropylene.

mm %: 94.2%; Molecular Weight: 65000.

COMPARATIVE EXAMPLE 2

Propylene was polymerized in the same manner as in Example 1, except for replacing isopropylidene(4- methylcyclopentadienyl)(3'-t-butylindenyl)zirconium dichloride with dimethylsilylbis(2,3,5-trimethylcyclopentadienyl)zirconium dichloride (a 100% racemic modification). There was obtained 23 g of isotactic polypropylene.

mm %: 98.3%; Molecular Weight: 99800.

The occurrence of chemical inversion in the polypropylene obtained in Examples 1 to 3 and Comparative Examples 1 and 2 was determined by a $^{13}$BC-NMR analysis according to a known method described in literature (*Macromolecules*, Vol. 21, p. 617 (1988)). The results obtained are shown in Table 1 below.

TABLE 1

| Example No. | The Number of Chemical Inversions per 1000 Monomer Units |
| --- | --- |
| Example 1 | 3.6 |
| Example 2 | 2.1 |
| Example 3 | 2.0 |
| Compara. Example 1 | 4.6 |
| Compara. Example 2 | 4.0 |

EXAMPLE 4

Propylene was polymerized in the same manner as in Example 2, except for replacing isopropylidene(4-t-butylcyclopentadienyl)(3'-t-butylindenyl)zirconium dichloride with a mixture thereof with its stereoisomer (purity: 60%). There was obtained 25 g of highly isotactic polypropylene.

mm %: 99.6%.

COMPARATIVE EXAMPLE 3

Propylene was polymerized in the same manner as in Example 2, except for replacing isopropylidene(4-t-butylcyclopentadienyl)(3'-t-butylindenyl)zirconium dichloride with an isomeric mixture of dimethylsilylbis(2,3,5-trimethylcyclopentadienyl)zirconium dichloride (racemic modification/meso form: 60%). There was obtained 30 g of a mixture of isotactic polypropylene and atactic polypropylene.

mm %: 78.5%.

EXAMPLE 5

In a 200 ml flask having been purged with argon was charged 100 ml of dehydrated toluene, and 7 ml of a 2.65 mol/l toluene solution of methylaluminoxane and a toluene solution of 0.02 mmol of isopropylidene(4-t-butylcyclopentadienyl)(3'-t-butylindenyl)zirconium dichloride were added thereto, followed by stirring at 40° C. for 10 minutes. To the solution was added 20 ml of 4-methylpentene-1, and polymerization was conducted at 40° C. for 3 hours to obtain 12.7 g of highly isotactic poly(4-methylpentene-1).

COMPARATIVE EXAMPLE 4

4-Methylpentene-1 was polymerized in the same manner as in Example 5, except for replacing isopropylidene(4-t-butylcyclopentadienyl)(3'-t-butylindenyl)zirconium dichloride with zirconocene dichloride, to obtain 9 g of atactic poly(4-methylpentene-1).

EXAMPLE 6

Polymerization reaction was carried out in the same manner as in Example 5, except for replacing 4-methylpentene-1 to be polymerized with 20 ml of 1,5-hexadiene, to obtain 16 g of a cyclized polymer.

EXAMPLE 7

Polymerization reaction was carried out in the same manner as in Example 5, except for replacing 4-methylpentene-1 to be polymerized with 20 ml of 1,7-hexadiene, to obtain 9 g of a polymer.

EXAMPLE 8

Preparation of Catalyst

Process A

In a 100 ml flask having been purged with nitrogen was charged 2 g of silica ("DAVISON 955"; sintered at 600° C. for 8 hours), and 20 ml of dehydrated toluene was added thereto to prepare a slurry. To the slurry was added 0.3 ml of a 2.5 mol/l toluene solution of methylaluminoxane (produced by TOSO AKUZO CO., LTD.), followed by allowing the mixture to react at room temperature for 1 hour. The solvent was removed by distillation under reduced pressure. To the residue was added 7.5 ml of a 1 mmol/l hexane solution of isopropylidene(4-t-butylcyclopentadienyl)(3'-t-butylindenyl)zirconium dichloride as prepared in Example 2, and the mixture was allowed to react for 1 hour, followed by drying under reduced pressure to obtain a solid catalyst (designated A type).

Copolymerization

In a 1.5 l SUS-made autoclave having been thoroughly purged with nitrogen were charged 70 mg of the above-prepared A type catalyst, 3.5 ml of a 0.5 mol/l hexane solution of triisobutylaluminum, and 800 ml of isobutane. To the mixture was introduced ethylene and 27 g of 1-hexene, and polymerization was conducted under an ethylene pressure of 3 kg/cm$^2$ at 70° C. After 1 hour, the reaction system was purged to cease the polymerization.

EXAMPLES 9 AND 10

Preparation of Catalyst

Process B

A solid catalyst component was prepared in the same manner as in Process A described in Example 8, except for using silica having been treated in hexane with 0.6 mmol of triethylaluminum per gram of silica and changing the amounts of methylaluminoxane and the complex as shown in Table 2 below (designated B type).

Copolymerization

Ethylene and 1-hexene were copolymerized in the same manner as in Example 8, except for using the above-prepared B type catalyst.

EXAMPLES 11 AND 12

Ethylene and 1-hexene were copolymerized in the same manner as in Example 8 or 9, except for using A type or B type catalyst prepared by using alumina as a carrier and changing the amounts of the complex and methylaluminoxane as shown in Table 2 below.

EXAMPLE 13

Ethylene and 1-hexene were copolymerized in the same manner as in Example 8, except for replacing silica as a carrier with magnesia and changing the amounts of methylaluminoxane and the complex catalyst as shown in Table 2 below.

EXAMPLE 14

Ethylene and 1-hexene were copolymerized in the same manner as in Example 8, except for replacing silica as a carrier with boron oxide and changing the amounts of methylaluminoxane and the complex catalyst as shown in Table 2 below.

Each of the ethylene/1-hexene copolymers prepared in Examples 8 to 14 was press molded at 190° C. The resulting molded article was excellent in transparency in every case.

COMPARATIVE EXAMPLE 5

Ethylene and 1-hexene were copolymerized in the same manner as in Example 8, except for replacing the catalyst used in Example 8 with zirconocene dichloride having the composition shown in Table 2 below (prepared by Process A).

Each of the catalysts used in Examples 8 to 14 and Comparative Example 5 was evaluated for activity in terms of specific rate (RSP) calculated by dividing an amount (g) of polymers produced with 1 g of the catalyst component for 1 hour, by the ethylene pressure (atm) in the reaction system. Further, physical properties of each of the ethylene/1-hexene copolymers obtained in these Examples were measured. The results obtained are shown in Table 2.

It is seen from the results that linear low-density ethylene copolymers having a high molecular weight and a mono-model melting point can be obtained by the use of the metallocene of the present invention.

EXAMPLE 15

The catalyst used in Example 8 was preserved in an ampule containing nitrogen for a long time, and the change in activity in terms of RSP (per gram of methylaluminoxane) was observed with time. The results obtained are shown in Table 3 below.

COMPARATIVE EXAMPLE 6

The change in activity of the catalyst used in Comparative Example 5 was observed with time in the same manner as in Example 15. The results obtained are shown in Table 3 below.

TABLE 3

| Example No. | RSP (per gram of Methylaluminoxane) (g/g · hr · atm) | | |
|---|---|---|---|
| | On The Day of Preparation | After 4 Days' Preservation | After 10 Days' Preservation |
| Example 15 | 560 | 550 | 380 |
| Compara. Example 6 | 102 | 40 | 8 |

It is seen from the results in Table 3 that the catalyst of the present invention exhibits good stability.

EXAMPLE 16

Ethylene and 1-hexene were copolymerized in the same manner as in Example 8, except for conducting polymerization in the co-presence of hydrogen. The resulting ethylene copolymer had an MFR of 2.3.

According to the present invention, the asymmetric metallocene of formula (I) can be used as a catalyst component for olefin polymerization without requiring any treatment for separation of an isomer, such as a high technique of fractional crystallization, to produce an industrially valuable poly-α-olefin with very high stereospecificity and reduced chemical inversion in its polymer chain at good efficiency.

Further, by using a solid catalyst composed of the asymmetric metallocene of the present invention and an organoaluminumoxy compound as supported on an inorganic oxide carrier in combination with an organoaluminum component as a co-catalyst, an ethylene-α-olefin copolymer having a high molecular weight and a low and mono-modal melting point (this means that the copolymer has a narrow composition distribution) can be obtained with good activity per unit organoaluminumoxy component.

While the invention has been described in detail and with reference to specific examples thereof, it will be apparent to one skilled in the art that various changes and modifications can be made therein without departing from the spirit and scope thereof.

TABLE 2

| Example No. | Process of Catalyst Preparation | Composition of Solid Catalyst (reduced to gram/gram-carrier) | | | Catalyst Activity A*2 (g/g · hr · atm) | Catalyst Activity B*3 (g/g · hr · atm) | MFR | HLMI | Melting Point (°C.) | SCB |
|---|---|---|---|---|---|---|---|---|---|---|
| | | Carrier (g) | Complex (g) | MAO*1 (g) | | | | | | |
| Example 8 | A | silica 1 | 0.043 | 0.5 | 6600 | 560 | n.f.*4 | 0.045 | 120 | 18 |
| Example 9 | B | silica 1 | 0.017 | 0.1 | 5000 | 470 | n.f. | 0.021 | 118 | 19 |
| Example 10 | B | silica 1 | 0.034 | 0.2 | 4080 | 698 | n.f. | 0.028 | 115 | 21 |
| Example 11 | A | alumina 1 | 0.034 | 0.2 | 1740 | 290 | n.f. | 0.016 | 114 | 21 |
| Example 12 | B | alumina 1 | 0.034 | 0.2 | 2220 | 380 | n.f. | 0.035 | 117 | 20 |
| Example 13 | A | magnesia 1 | 0.034 | 0.2 | 1050 | 170 | n.f. | 0.041 | 117 | 19 |
| Example 14 | A | boron oxide 1 | 0.034 | 0.2 | 1900 | 360 | n.f. | 0.049 | 116 | 19 |
| Compara. Example 5 | A | silica 1 | 0.034 | 0.2 | 617 | 102 | 75.4 | — | 123 | 10 |

Note:
*1 Methylaluminoxane
*2 RSP (per gram of the complex)
*3 RSP (per gram of methylaluminoxane)
*4 The sample did not melt to flow.

What is claimed is:

1. A metallocene represented by formula (I) and its enantiomer:

(I)

wherein M represents a transition metal selected from Ti, Zr, and Hf; $X^1$ and $X^2$, which may be the same or different each represents a hydrogen atom, a hydrocarbon group containing from 1 to 10 carbon atoms, an alkylsilyl group, an arylsilyl group, or a halogen atom; $R^1$, $R^2$, $R^3$, $R^6$, and $R^7$ each represents a hydrogen atom, a hydrocarbon group containing from 1 to 10 carbon atoms, an alkylsilyl group, or an arylsilyl group, provided that either one of $R^1$ and $R^2$ is not a hydrogen atom; $R^4$ and $R^5$ each represents a hydrocarbon group containing from 1 to 10 carbon atoms, an alkylsilyl group, or an arylsilyl group, or they are connected together to form a ring; Y represents a carbon atom, a silicon atom, or a germanium atom; and n represents an integer of from 1 to 3.

2. The metallocene and its enantiomer as claimed in claim 1, wherein Y is a carbon atom.

3. The metallocene and its enantiomer as claimed in claim 1, which is a compound represented by formula (II) and its enantiomer:

(II)

wherein M, $X^1$, $X^2$, $R^1$, $R^2$, $R^3$, $R^6$, $R^7$ and n are as defined in formula (I); and Y' represents a carbon atom.

4. The metallocene and its enantiomer as claimed in claim 3, wherein M is hafnium.

5. The metallocene and its enantiomer as claimed in claim 1, which is a zirconocene represented by formula (III) an its enantiomer:

(III)

wherein $X^1$, $X^2$, $R^1$, $R^2$, $R^3$, $R^6$, and $R^7$ are as defined in formula (I); and Y' represents a carbon atom.

6. The metallocene and its enantiomer as claimed in claim 1, wherein $R^1$ represents a hydrogen atom.

7. The metallocene and its enantiomer as claimed in claim 2, wherein M is Zr.

* * * * *

UNITED STATES PATENT AND TRADEMARK OFFICE
CERTIFICATE OF CORRECTION

PATENT NO. : 5,329,031
DATED : July 12, 1994
INVENTOR(S) : Miyake et al

Page 1 of 2

It is certified that error appears in the above-indentified patent and that said Letters Patent is hereby corrected as shown below:

the Abstract; Column 3, lines 9-22; and Column 17, lines 16-19, delete  and insert Column 4, lines 1-15 and Column 18, lines 1-16, delete  and insert

UNITED STATES PATENT AND TRADEMARK OFFICE
CERTIFICATE OF CORRECTION

PATENT NO. : 5,329,031
DATED : July 12, 1994
INVENTOR(S) : Miyake et al

Page 2 of 2

It is certified that error appears in the above-indentified patent and that said Letters Patent is hereby corrected as shown below:

Column 8, lines 13-15, delete $R_2^8Al-(O-Al)_m-R_2^8$ with branch $R^8$  and insert $R^8_2Al-(O-Al)_m-R^8_2$ with branch $R^8$ Signed and Sealed this Tenth Day of January, 1995

Attest:

BRUCE LEHMAN

Attesting Officer

Commissioner of Patents and Trademarks